United States Patent
Nigam et al.

[19]

[11] Patent Number: 5,891,048
[45] Date of Patent: Apr. 6, 1999

[54] SIGNAL DETECTOR

[75] Inventors: Indra B. Nigam, Lake Oswego, Oreg.; Max Schaldach, Erlangen, Germany

[73] Assignee: Biotronik Mess- und Therapiegeraete GmbH & Co. Ingenieurbuero Berlin, Berlin, Germany

[21] Appl. No.: 878,486

[22] Filed: Jun. 18, 1997

[30] Foreign Application Priority Data

Jun. 18, 1996 [DE] Germany ................. 196 26 353.0

[51] Int. Cl.$^6$ .................................................. A61B 5/0456
[52] U.S. Cl. ........................................... 600/521; 128/901
[58] Field of Search ................... 128/901, 902; 600/509, 517, 521; 607/4, 5, 9

[56] References Cited

U.S. PATENT DOCUMENTS

| | | | |
|---|---|---|---|
| 4,240,442 | 12/1980 | Andersen et al. | 600/521 |
| 4,940,054 | 7/1990 | Grevis et al. | |
| 5,117,824 | 6/1992 | Keimel et al. | |
| 5,339,820 | 8/1994 | Henry et al. | |
| 5,513,644 | 5/1996 | McClure et al. | 600/521 |
| 5,620,466 | 4/1997 | Haefner et al. | 607/5 |
| 5,658,317 | 8/1997 | Haefner et al. | 607/5 |
| 5,662,688 | 9/1997 | Haefner et al. | 607/5 |

FOREIGN PATENT DOCUMENTS 2805482 8/1979 Germany .

*Primary Examiner*—William E. Kamm
*Assistant Examiner*—George R. Evaniswo
*Attorney, Agent, or Firm*—Venable; George H. Spencer; Catherine M. Voorhees

[57] ABSTRACT

A signal detector for detecting a biosignal with approximately known morphology in a complex input signal (ECG), in particular for the detection of QRS complexes in an electrocardiogram. The detector has circuitry for detecting the maximum amplitude (PEAK) of the detected signal complex within a predetermined time window, with a threshold value discriminator, a detector parameter preselection circuit for determining an initial value for the detector parameter characterizing the detector sensitivity, which parameter determines the detector threshold value when responding to a detection signal in dependence on the maximum amplitude and a detector parameter timing circuit for adjusting a predetermined time dependence of the detector parameter and thus the detection threshold value. The predetermined time dependence has at least in a first time domain a step-by-step reduction of the detection threshold value up to a lower limit value that is determined in dependence on the maximum amplitude and/or in a second time domain a step-by-step increase with preset steps (STEPS) up to an upper limit value determined in dependence on the maximum amplitude.

8 Claims, 6 Drawing Sheets

SIGNAL DETECTOR

CROSS-REFERENCE TO RELATED APPLICATION

This application claims the priority of patent application Ser. No. 196 26 353.0-35 filed in Germany on Jun. 18, 1996, the subject matter of which is incorporated herein by reference.

BACKGROUND OF THE INVENTION

The present invention relates to a signal detector for detecting specific biosignals, in particular for detecting QRS complexes or P-waves in an electrocardiogram.

The detection of specific biosignals in a disturbed signal train is a problem of high diagnostic and therapeutic relevance, e.g. in the field of cardiology and neurology. Thus, the identification of the individual segments of an electrocardiogram—the P-wave originating with the auricle, the QRS complex originating with the heart chamber and, if necessary, also the T-wave of the electrocardiogram that originates with the chamber—as well as the correct determination of the time interval between signal segments with the same origin are of central importance to the detection and successful treatment of arrhythmias, specifically for the classification of tachyarrhythmias and the correct function of pacemakers and defibrillators.

In the simplest case, the detection of the QRS complex in an ECG signal occurs through a comparison of the ECG signal with a predetermined threshold value, which is above an assumed level of signals with a different origin. If the ECG signal exceeds the threshold value, a detection signal indicating the appearance of a QRS complex is emitted.

One problem in this case is that the signal level of the ECG signal is subject to fluctuations, which can lead to false detections.

The fact that the QRS complexes can have very different amplitudes for certain arrhythmias and in the course of a pacemaker therapy is taken into account according to U.S. Pat. No. 4,940,054 by programming in three different sensitivity or threshold values as well as a preset sequence for the use of these varied threshold values. However, this solution has a very limited potential and is hardly advantageous, particularly for a fluctuating interference signal level.

A QRS detector with automatic threshold value adaptation is described in German Patent 2 805 482, for which the detection threshold for the amplitude of the R-waves follows and, after a R-wave appears, is lowered exponentially in each case with a time constant that is predetermined by the components of the analog circuit. This solution is also very inflexible, owing to the fixed time behavior on the component side.

A R-wave detector is described in U.S. Pat. No. 5,117,824, for which the detection threshold automatically follows the R-wave amplitude and in each case is lowered linearly, starting with the moment a R-wave appears until the following R-wave appears. The initial threshold value is then set again to a predetermined share of its amplitude. However, a R-wave evoked by a pacemaker pulse is ignored, and the linear lowering is continued for a predetermined time interval to be able to detect possibly following R-waves with low amplitude (such as can occur with tachyarrhythmias induced by pacemakers). However, this solution also has little adaptability to the various use/interference signal constellations.

The signal detector shown in U.S. Pat. No. 5,339,820 has a refractory interval, and the detection sensitivity is adjusted automatically. If a predetermined initial detection threshold (detection event) is exceeded, the signal detector starts a refractory interval, during which no further detection events can occur, so as to prevent that an individual QRS complex is detected falsely more than once. In addition, the signal detector determines the amplitude for the QRS complex during the refractory interval. The threshold value is subsequently set to a new value (preferably 75% of the amplitude) in dependence on the previously determined QRS complex amplitude. Subsequently, the threshold value is lowered step-by-step with a timing control. The lowering of the threshold value stops if either the following QRS complex is detected or the threshold value has reached a preprogrammed lower limit value.

However, the input signal fluctuations often do not or not only impact the specific useful signal, but (also) other signals, among other things interference signals. In such a case, it can occur that the known signal detector lowers the threshold value below the level of the nonspecific signals, which leads to false detections. In addition, a method which provides exclusively for the lowering of the detection threshold is not sufficiently differentiated for a detection of specific signals in complex signal sequences.

It is therefore the object of the invention to create a signal detector of the aforementioned type, which permits an automatic adjustment of the detection sensitivity or amplification to avoid false detections for a fluctuating level of the useful signal as well as the interference signal segments and which also allows a detection of specific useful signals within complex signals.

SUMMARY OF THE INVENTION

With the above objects in view, the present invention resides in a signal detector for detecting a biosignal with nearly known morphology in a disturbed input signal (ECG), in particular for detecting QRS complexes in an electrocardiogram, which detector comprises a detector input for receiving the input signal (ECG) and a detector output for emitting a detection signal (DETECT) that indicates the detection of the biosignal in the input signal; a threshold value discriminator connected on the signal side with the detector input for comparing the input signal (ECG) with the detection threshold value and for emitting the detection signal (DETECT) if the threshold value is exceeded by the input signal; a device connected via a signal input with the detector input and via a control input with the threshold value discriminator output and functions to detect the maximum amplitude of the detected signal complex during a predetermined time window, following the output of the detection signal (DETECT); a detector parameter pre-selection circuit that is connected via a signal input with the amplitude detection device and via a control input with the threshold value discriminator and, on the output side, at least indirectly with the control input of the threshold value discriminator, used to determine an initial value for a detector parameter characterizing the detector sensitivity, which detector parameter determines the detection threshold value by responding to the detection signal and in dependence on the maximum amplitude (PEAK); a detector parameter timing circuit connected on the output side with the control input of the threshold value discriminator and is used to adjust a predetermined time dependence of the detector parameter and thus also the detection threshold value, starting with the initial value, wherein the predetermined time dependence comprises in a first time domain a step-by-step reduction of the detection threshold value up to at most a lower limit value that is determined in dependence on the maximum amplitude (PEAK), and/or in a second time domain, a step-by-step increase with predetermined steps (STEPS) up to at most an upper limit value determined in dependence on the maximum amplitude.

By virtue of the above features, the present invention provides the technology to determine the amplitude of the relevant signal segment for a detecting event, to determine a new starting value for the detection sensitivity in dependence on this and to subsequently imprint a time dependence on it, until another relevant signal segment is detected or the detection sensitivity has reached an upper limit value that depends on the amplitude of the preceding useful signal. The detection sensitivity can be adjusted here to discrete levels, on the one hand by changing the input amplification and on the other hand by changing the threshold value, wherein the time-dependence can comprise one or several segments with increasing and/or one or several segments with decreasing sensitivity.

The term input signal is to be understood to be a general term and comprises, among other things, all electrical signals that reflect an optional biological state quantity. In particular, the input signal is an ECG signal picked up via the electrodes of an implanted heart diagnosis and/or therapy device (pacemaker, cardioverter, defibrillator, ECG probe), where the QRS complexes caused by—in particular spontaneous—heart actions or even P-waves must be detected as specific biosignal.

The terms input and output or input signal and output signal in this case do not mean that the signal detector according to the present invention is necessarily an independent device, which is connected to other devices only for the purpose of a data exchange. Rather, the signal detector according to the present invention is also suited for integration into other devices, e.g. an implantable pacemaker. Input and output can in that case be a component of a data interface realized purely with software.

One advantageous embodiment of the invention provides for a blocking element, which blocks during a predetermined time interval—blank-out or refractory time ("holdoff time")—the emitting of further detection signals and thereby prevents the multiple detection of an individual signal complex.

Following a detection event, the signal detector according to the present invention additionally—or also alternatively—increases the threshold value to prevent a subsequent false detection, e.g. of a T-wave. The increase in the threshold value here is linked to the amplitude of the previously detected signal complex in order to adapt the threshold value to the input signal level. The circuit is therefore provided with means for determining the maximum value for the input signal occurring within a predetermined time interval—in the following also called a measuring time interval—after the appearance of the detection signal. The increased threshold value is calculated from this and—in a useful modification—is recorded in a threshold value memory. For one preferred embodiment, the threshold value for a detection event is in each case raised to the amplitude of the detected signal complex. However, it is also possible to increase the threshold value to another amplitude function value. It is only crucial that the threshold value is adapted to the amplitude of the previously detected signal complex.

The measuring time interval, during which the maximum input signal value is determined, in this case preferably lies within the refractory time and must be sufficiently long to comprise the highest amplitude segment of the signal complex. When detecting QRS complexes in an ECG signal, a measuring time interval of 70 to 100 ms has proven to be suitable in view of the maximum duration of a R-wave.

However, the maximum value of the detected signal complex is used not only to calculate the new, increased threshold value, but is additionally used to calculate a variable limit value at which a subsequent reduction of the threshold value stops, so as to prevent the threshold value from dropping below the level of interference signals. It can be stored temporarily for this in an amplitude memory.

Following the measuring time interval, the threshold value is lowered in the direction of this limit value. The circuit comprises here in particular an arithmetic unit, which respectively calculates from the actual threshold value a correspondingly reduced threshold value for the following lowering stage and records this in the threshold value memory.

In accordance with one variant of the invention, the reduction of the threshold value occurs step-by-step, controlled by a clock generator in that the arithmetic unit calculates for each pulse from the clock generator a new threshold value from the actual threshold value and stores it. For the detection of QRS complexes in an ECG signal, it has proven advantageous to lower the threshold value in time intervals of respectively 82 ms during a measuring in the atrium or 125 ms during a measuring in the ventricle. However, the time intervals respectively used for the reduction of the threshold value do not necessarily have to be constant. Rather, for a step-by-step reduction of the threshold value, it is often advantageous to adapt the width of the steps to the amplitude of the preceding signal complex, so that the threshold value can be reduced rapidly from the relatively high initial value following a "strong" signal complex, whereas it is possible to reduce the threshold value slowly, following a "weak" signal complex.

It is possible, for example, to calculate the new threshold value in that the arithmetic unit decrements the actual threshold value by a predetermined amount. It is particularly advantageous, however, if the calculation is carried out in a manner that the actual threshold value is multiplied with a predetermined factor to calculate the new threshold value. A rapid reduction of the threshold value can be achieved in this way, which is particularly important if signal complexes with an especially high amplitude appear at random, so that the detection sensitivity for detecting the subsequent signal complex with normal amplitude is sufficient.

The lowering of the threshold value stops with the following detection event, meaning if the input signal exceeds the threshold value and the threshold value discriminator or the comparator unit generates a detection signal.

The detector circuit has at least one limiter to prevent an excessive lowering of the threshold value in case the following detection event does not occur. The lower limiting value where the reduction of the threshold value is stopped by the limiter is in this case calculated with an arithmetic unit from the maximum value of the previously detected signal complex, which is stored in the amplitude memory. For the detection of QRS complexes in an ECG signal, it has proven advantageous to stop the reduction of the threshold value at a level that corresponds to 25% of the amplitude of the previously detected QRS complex.

Thus, the signal detector according to the present invention increases the threshold value following a detection event and subsequently reduces the threshold value again.

During the reduction of the threshold value, the initial as well as the final threshold value are in this case linked to the amplitude of the preceding QRS complex.

For one advantageous, modified variant of the invention, the final value when reducing the threshold value is not only linked to the amplitude of the last signal complex, but also to the amplitudes of preceding signal complexes. The signal detector has several storage elements for this, which respectively serve to store the amplitude of one signal complex. In one preferred embodiment of this modification, this is realized with a shift register comprising several storage locations. During the detection of a new signal complex, its amplitude is then "inserted" as a new value into the shift register. The oldest amplitude value is simultaneously pushed out of the shift register. All storage elements in this case are connected to the associated arithmetic unit, which calculates the variable lower limit value in dependence on the stored amplitude values, wherein the amplitude values preferably are weighted according to their preceding determination. Thus, more weight should be given to the amplitudes of the immediately preceding signal complexes than to the amplitudes of older signal complexes.

For the last mentioned variant, the effect of an "outlier" is reduced advantageously. Also, the threshold value adaptation to the signal level of the input signal is more exact since several amplitude values better reflect the actual signal level, than a single amplitude value. The initial value for the detection threshold effective at the start of the reduction can be adapted in the same way to the amplitudes of several consecutive signal complexes.

One preferred embodiment provides for another limiter in addition to the previously mentioned limiter, which prevents a dropping of the threshold value below a predetermined (absolute) lower limit value, regardless of the amplitude for the preceding signal complex.

The signal detector described in the above is advantageously suited to be realized within the framework of a software-type solution, in particular as a component of a microprocessor-controlled pacemaker or defibrillator. However, it is not limited primarily to a software realization, but can also be configured with hardware only or in a combination of hardware components and a software-realized control.

The signal detector according to the present invention is not limited to a separate design of the above described modules or structural components. Thus, the individual arithmetic devices, for example, can be components of an arithmetic unit (ALU—arithmetic logical unit). Also, the various control units or regulating circuits can be combined in one module. It is only important that the above described technical function is made available.

BRIEF DESCRIPTION OF THE DRAWINGS

These and other features and advantages of the invention will be further understood from the following detailed description of the preferred embodiments with reference to the accompanying drawings in which.

DETAILED DESCRIPTION OF THE PREFERRED EMBODIMENTS

Figure 1:
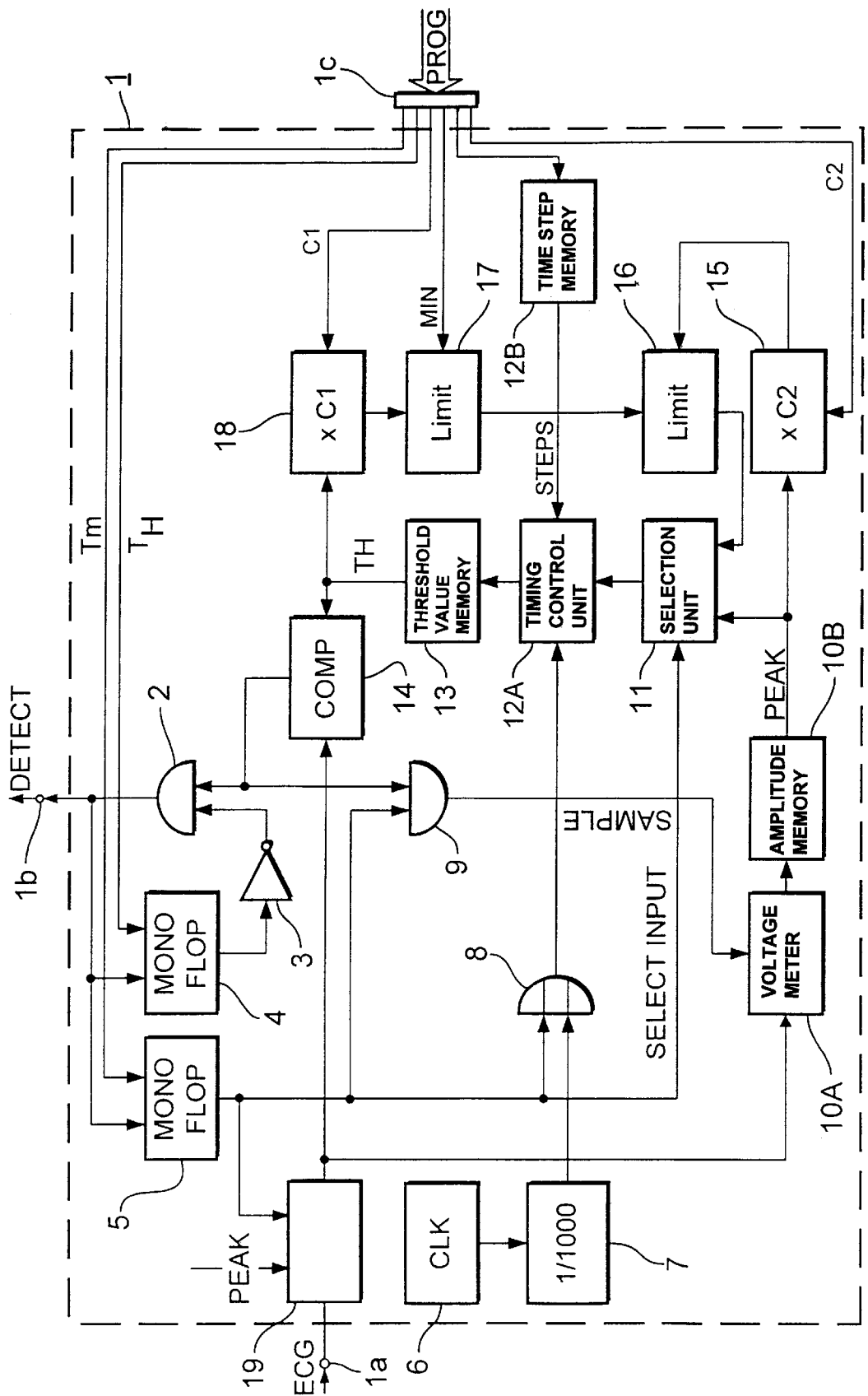
FIG. 1 shows a block wiring diagram as a preferred exemplary embodiment of the invention that represents a signal detector for detecting QRS complexes in an electrocardiogram.

The signal detector 1 shown in FIG. 1 constitutes a component of an implantable pacemaker and is used to detect QRS complexes supplied via a detector input 1a in an electrocardiogram ECG, which is picked up intracardially via the pacemaker electrodes. The QRS complexes are detected and a detection signal is emitted via an output 1b, on the one hand so that it is possible to inhibit the emission of stimulation pulses when heart actions occur spontaneously during the demand operation. On the other hand, it permits the determination of the heart rate and thus also the detection of arrhythmias, in particular tachycardias and the introduction of a suitable therapy mode.

Figure 2:
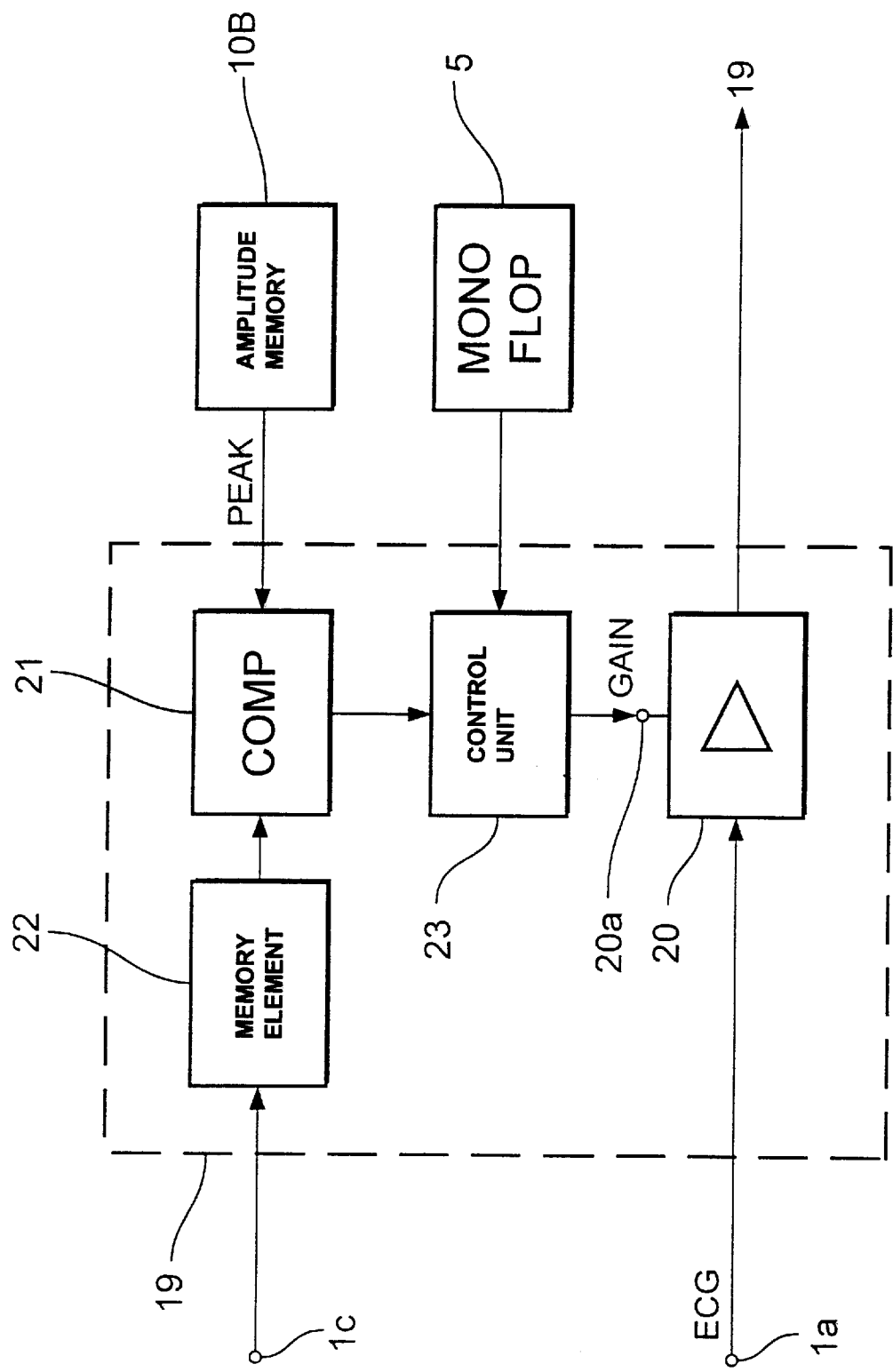
FIG. 2 shows the input stage for the signal detector shown in FIG. 1 as block wiring diagram.

In order to pick up the ECG signal, the signal detector 1 has an input stage 19 connected to the input 1a, which input stage is shown in more detail in FIG. 2 and amplifies the ECG signal, so as to simplify the following detection. The output signal from the input stage 19 is supplied to a comparator unit (a threshold value discriminator) 14 where it is compared with a threshold value, previously stored in a threshold value memory 13. If the ECG signal amplitude is below the threshold value, then the output signal from the threshold value discriminator 14 assumes a low level, which is transmitted via an AND-gate 2 to the output 1b of the signal detector 1. As described in detail below, the detection sensitivity in this case is raised step-by-step to permit the detection of QRS complexes with a low amplitude.

For this, the actual threshold value stored in the threshold value memory 13 is initially fed to an arithmetic unit 18, which calculates a correspondingly reduced threshold value through multiplication with a predetermined factor C1. The output signal from arithmetic unit 18—the reduced threshold value—is fed to a first limiter 17, which limits the threshold value downward to a limit value MIN that is predetermined through programming (via a programming connection 1c). Independent of the reduced threshold value calculated with the arithmetic unit 18, the output signal from the limiter 17 is therefore at least equal to the lowest limit value MIN, which effectively prevents a false detection of interference signals.

The output signal from the first limiter 17 is supplied to a second limiter 16, which limits the threshold value once more downward. The minimum value adjusted in the limiter 16 is, however, not constant, but depends on the amplitude of the last QRS complex, which is determined anew for each detection with a voltage meter 10A and is stored in an amplitude memory 10B. The amplitude for the last QRS complex is read out of the amplitude memory 10B and fed to a second arithmetic unit 15, which calculates the actual minimum value for the limiter 16 through multiplication with a factor C2. If the value for C2 is 0.25 for example, then the second limiter 16 prevents the threshold value from dropping below one fourth the value for the amplitude of the last detection event.

The threshold value limited in this way is then supplied to a selection unit 11 and from there is transmitted to a control unit 12, which is designed to provide a timed control of a step-by-step reduction in the threshold value. The signal detector has a pulse generator G for this, the high-rate pulse signal of which is supplied by way of a frequency divider 7 and the OR-gate 8 to a timing control unit 12A. This timing control unit also has a time step memory 12B that can be programmed via the programming input 1c and records the reduced threshold value present at its input in the threshold value memory 13 by clocking it with the internal clock generator and in accordance with a time sequence for adjusting the threshold value, which sequence is stored in the time step memory 12B. Immediately following this recording operation, the detection sensitivity of the signal detector is adjusted in accordance with the new threshold value. A new threshold value is calculated at the same time in the above described manner and, following completion of the time interval planned in the stored time sequence for the new step, is again recorded in the threshold value memory 13. Thus, the threshold value is reduced step-by-step, respectively by the factor C1, until either the first limiter 17 prevents a dropping of the threshold value below the absolute minimum value or the second limiter 16 becomes active to prevent a dropping of the threshold value below C2-times the amplitude of the last QRS complex.

In addition to the two aforementioned opt-out conditions, the programmed lowering of the threshold value is also stopped if a QRS complex is detected. That is the case if the ECG signal amplified in the input stage 19 exceeds the actual value stored in the threshold value memory 13, so that the output signal of comparator unit 14 assumes a high-level. On the one hand, the high level appearing at the output of comparator unit 14 is conducted via the AND-gate 2 to the output 1b where it is emitted as detection signal DETECT. On the other hand, it triggers a first monoflop 4 during the detection of a QRS complex, which then assumes a low level for a time interval—can also be programmed—$T_m$ (e.g. 121 ms). This monoflop is fed via an inverter 3 to the AND-gate 2 and blocks this gate, so that no additional detection signals can be emitted during the holding time for the monoflop 4, independent of the output signal from the comparator unit 14.

In addition, the output signal from the comparator unit 14 triggers a second monoflop 5, which subsequently assumes high level for a time interval $T_m$ that is also programmed (e.g. 86 ms). The monoflop 5 defines the time window according to a detection event, in which the voltage meter 10A that is designed as peak value detector is activated and determines the amplitude for the detected QRS complex.

For this, the comparator unit 14 continuously compares the amplitude of the ECG signal with the threshold value stored in the threshold value memory 13. If the threshold value is exceeded, the output signal at the comparator unit assumes high level, which is supplied to the two AND-gates 2, 9. While the AND-gate 2 blocks owing to the previously triggered MONOFLOP, the other AND-gate 9 switches through and transmits the output signal from the comparator unit to the voltage meter 10A. This voltage meter is connected on the output side with the amplitude memory 10B where it stores the maximum amplitude detected within the time window as actual maximum value. During the monoflop 5 holding time, the selection unit reads out the maximum value PEAK from the amplitude memory 10B—this differs from the previously described lowering of the threshold value—and transmits this value to the timing unit 12A, which is also triggered via the monoflop 5 and the OR-gate 8 and records the maximum value as new threshold value TH in the threshold value memory 13. (If the ECG signal again exceeds the threshold value stored in memory 13 during the holding time $T_m$ of the monoflop 5, the maximum value in memory 10B and the threshold value in memory 13—identical for the example at hand—are updated accordingly in the memory 13. The maximum value and the threshold value thus follow during the detection of a QRS complex until the holding time $T_m$ of monoflop 5 is completed.)

The maximum value PEAK stored in the amplitude memory 10B in this case is used—as already described—to calculate the lower limit value for the limiter 16 during the subsequent reduction of the threshold value to increase the detector sensitivity, and is therefore not changed again after the holding time for monoflop 5 is completed. This is achieved in that the output signal from comparator unit 14 is blocked by the AND-gate 9 following the completion of the monoflop 5 holding time, so that the memory 10B retains its value, regardless of the output signal from the comparator unit 14.

In contrast, the threshold value TH stored in the threshold value memory 13—as described in the above—is reduced step-by-step to increase the detection sensitivity.

Essential elements of the input stage 19 are shown in FIG. 2.

An amplifier 20 is provided to amplify the ECG signal that is picked up intracardially. The amplification factor of this amplifier can be adjusted to permit an adaptation to the signal level of the ECG signal. Thus, the amplification factor is adjusted in dependence on the amplitudes for the last QRS complexes, which are respectively stored in the amplitude memory 10B. For that reason the stored maximum value is fed to a comparator unit 21 and is compared there with a threshold value stored in a memory element 22. If the maximum value of the last QRS complex exceeds the predetermined threshold value, then the output signal for the comparator unit 21 assumes high level, which is supplied to an input stage control unit 23. This unit functions to adjust the amplification factor of the input amplifier 20 in dependence on the amplitudes of the last QRS complex. In this case, a change in the amplification factor always occurs—provided it is even necessary—once the maximum value of the up-to-date QRS complex has been determined. This is the case if the monoflop 5 holding time is completed and the monoflop assumes once more low level. The monoflop 5 therefore is connected to the control unit 23 and triggers this unit with the decreasing edge of the output signal, that is at the end of the holding time. The control unit 23 subsequently checks the output signal from the comparator unit 21.

If the comparator unit 21 supplies high level, then this means that the maximum value of the actual QRS complex exceeds the predetermined threshold value. In that case, the control unit 23 adjusts a reduced amplification factor since the ECG signal level is relatively high. In addition, for each triggering through the decreasing edge of monoflop 5, the control unit 23 stores the output signal from the comparator unit 21 internally (not shown here in more detail), so that the maximum values of the preceding QRS complexes can also be taken into account for the decision to change the amplification factor.

On the other hand, if the control unit 23 receives a low level from the comparator unit 21, this means that the actual QRS complex has a relatively low level. The control unit 23 in that case draws upon the internally stored output signals of the two preceding QRS complexes to make a decision concerning the change in the amplification factor. The current adjustment of the amplification factor is maintained if the maximum value of at least one of the two preceding QRS complexes has exceeded the predetermined threshold value. If, however, not only the maximum value of the current QRS complex falls below the predetermined threshold value, but also the maximum values for the two preceding QRS complexes, then the control unit 23 adjusts a higher amplification factor to permit an adaptation to the relatively low signal level of the ECG signal.

Thus, the amplification factor of the input amplifier 20 is reduced as soon as an individual QRS complex with high amplitude is detected, while the reduction in the amplification factor occurs only if three QRS complexes with low amplitude are detected successively.

The FIGS. 3a to 3d show, respectively, the course of a typical ECG signal as well as the threshold value of a signal detector according to various embodiments of the invention. The ECG signal is shown in each case as a continuous line and comprises three QRS complexes with relatively low amplitude and following that one or two QRS complexes with somewhat higher amplitude. The time-dependent course of the threshold value for the signal detector is shown as a dashed, bold line. In addition, the Figures respectively show the variable lower limit value for each threshold value as a thin, dashed line.

Figure 3A:
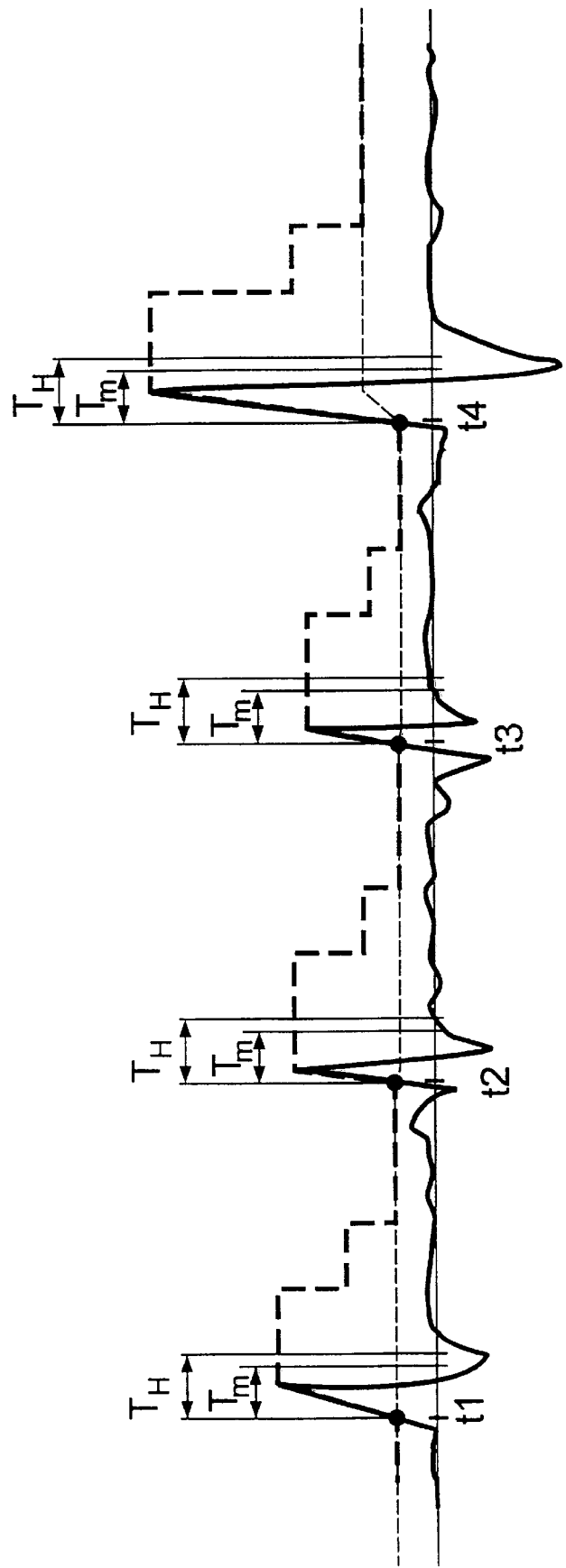
FIGS. 3a to 3d show examples of an electrocardiogram as well as the associated time-dependent course of the detection threshold for various embodiments of the invention.
Figure 3B:
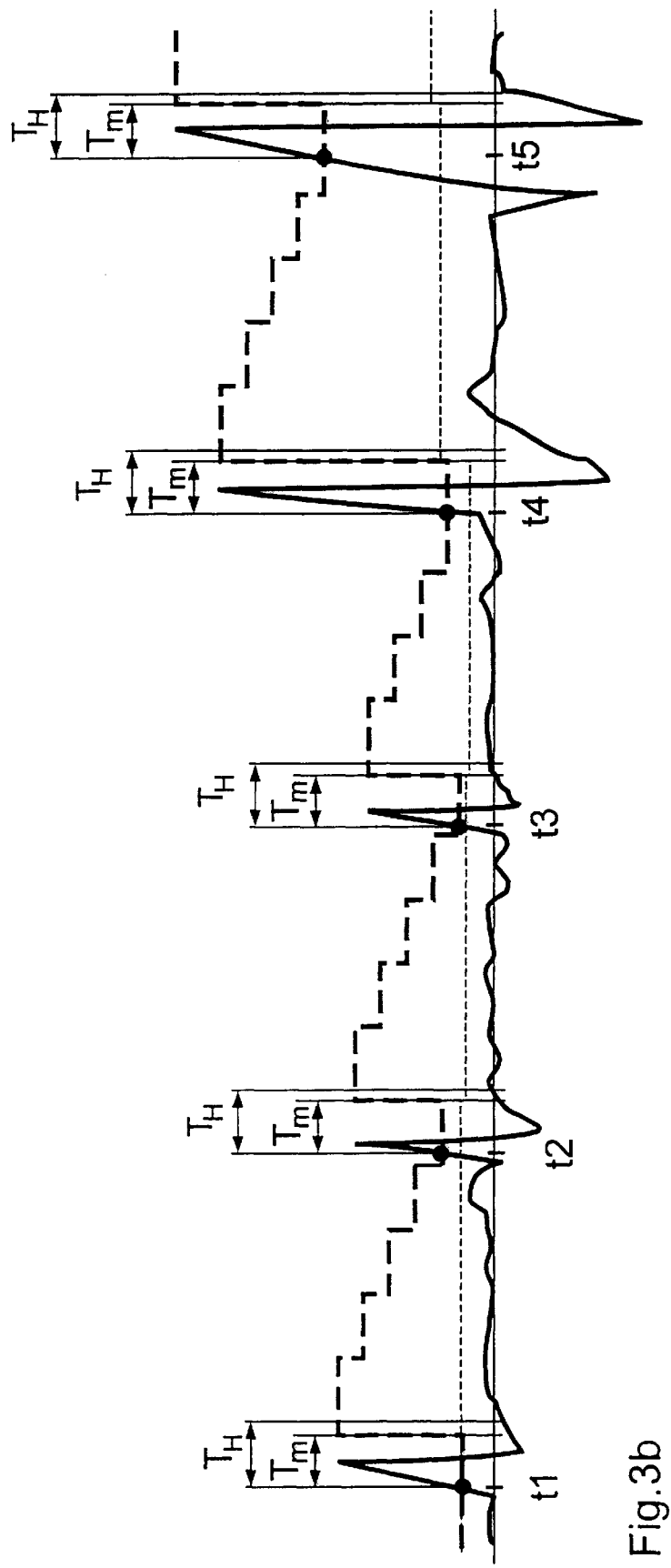
Figure 3C:
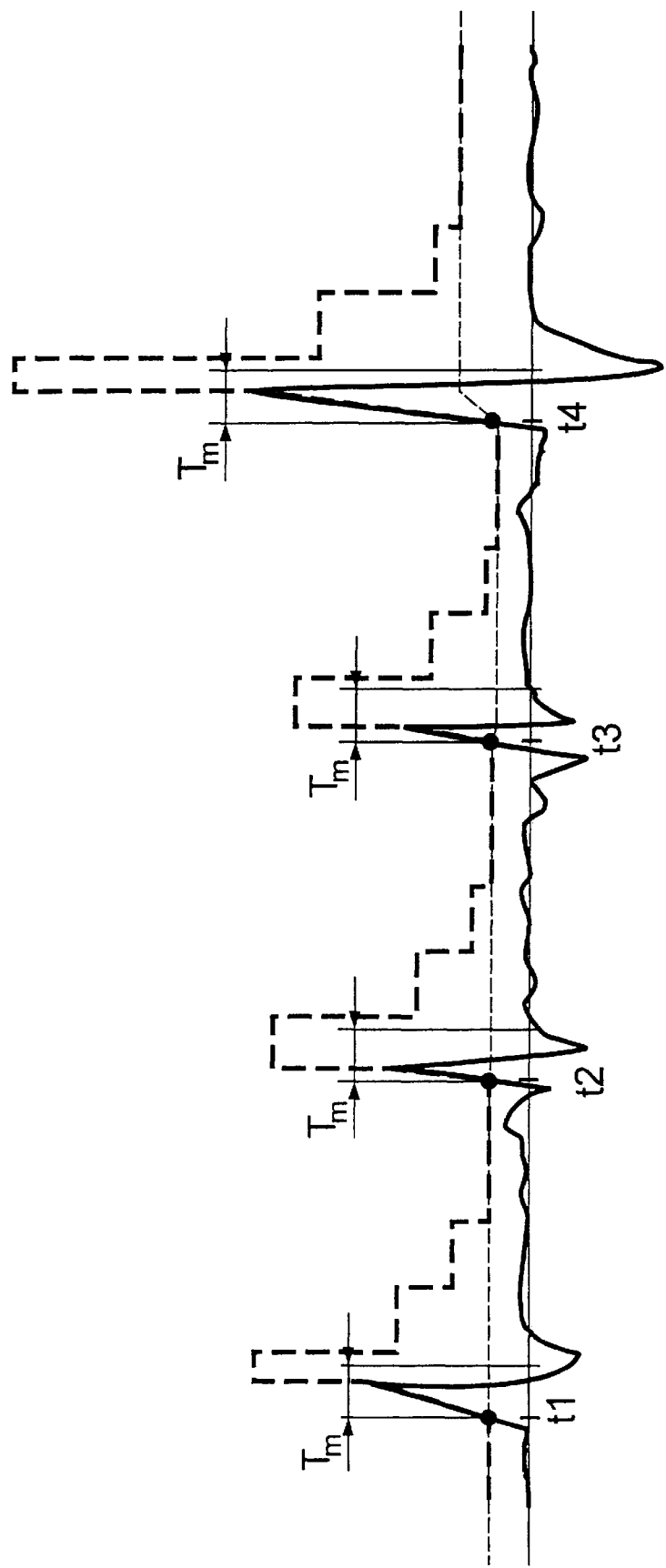
Figure 3D:
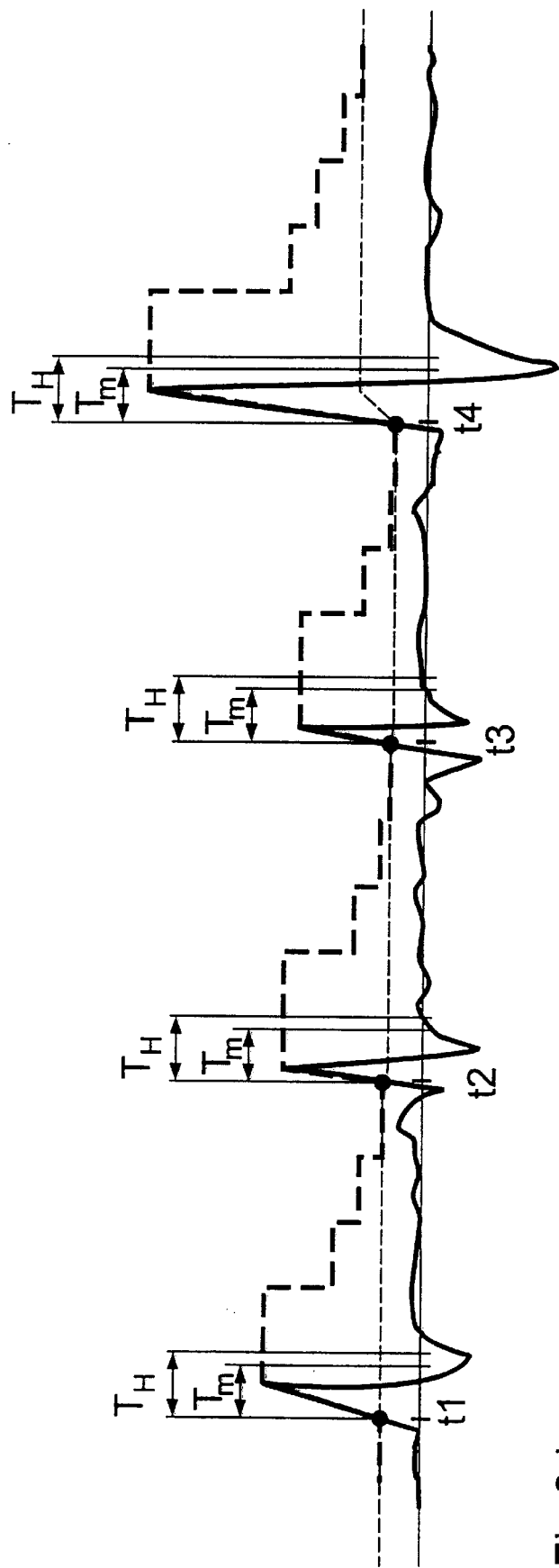

All figures are based on the actual, lower limit value. At point in time $t_1$, the ECG signal exceeds the threshold value, which results in a detection event (shown as a black dot). In FIGS. 3a, 3b and 3d, this is followed by the start of a blank-out or refractory time $T_H$ (holdoff time), during which no further detection signals are emitted to prevent a multiple detection of a QRS complex. No refractory time is provided for the FIG. 3c.

At the same time, each detection event starts a second time interval at points in time $t_1$ to $t_4$ or $t_5$ (measuring time window) $T_m$, during which the maximum signal amplitude is determined. In accordance with FIGS. 3a, 3c and 3d, the threshold value follows the ECG signal until the maximum value is reached, while the new setting of the detection threshold according to FIG. 3b does not take place until after the measuring time window is closed. A detection event initially leads to an almost jump-like reduction in the detection sensitivity. In accordance with FIGS. 3a, 3b, and 3d, the detection threshold in this case is increased to the maximum amplitude of the last detected R-wave, whereas FIG. 3c provides for a short-term, step-by-step increase that clearly exceeds this and allows the blanking out of artefacts, even without a customary absolute blank-out or refractory time.

Following this, the detection sensitivity is again increased step-by-step, meaning the threshold value is reduced correspondingly in steps. In accordance with FIG. 3a—corresponding to the above-described principle and referring to FIG. 1—this occurs in each case by cutting the preceding value in half for each new step; the same holds true according to FIG. 3c (after restoring the initial excessive threshold value); according to FIG. 3b this occurs in steps with constant amounts; and according to FIG. 3d by using a combination of the procedural steps taken in FIGS. 3a and 3c.

The starting point for all examples is the maximum amplitude value of the last QRS complex which can, however, also be multiplied with a predetermined factor or, if necessary, provided with a fixed increment or decrement for determining the initial value. For the arrangement according to FIG. 1, this must be realized via a corresponding configuration of the selection unit 11 or the timing unit 12.

The individual steps for all figures have the same width (time duration), e.g. 125 ms can be adjusted for those used for the QRS detection and 82 ms in an atrial detection channel. However, it is also possible to program in a threshold detection timing with steps of different duration, or for which the step length or duration is determined in dependence on the signal amplitude, in particular is amplified for weak signals.

The lowering of the threshold value is completed once it reaches the variable lowest limit value, shown as a thin, dashed line. The fixed programmed, absolute lowest limit value is not shown in the figures.

In addition to the two opt-out conditions named in the above, the reduction of the threshold value is also stopped—as shown in the Figures—if the signal detector detects the following QRS complex. In that case, the detection sensitivity is again increased almost jump-like, as described in the preceding.

The invention is not limited to the above described embodiments. Rather, a number of variants are conceivable, which make use of the solution shown even if the embodiments differ basically. Modifications for the specific detection of P-waves in a complex ECG can, for example, be useful, such that a longer-lasting increase in the detection threshold is initially realized following a predetermined time program, which increase exceeds the amplitude of the P-wave for blanking-out interfering chamber pulses—these may appear as distant field signals in the auricle—and a lowering for detecting the subsequent P-wave is not realized until later on.

Furthermore, it may be useful to make a distinction in how the above-sketched operation of a QRS detector is handled for spontaneous heart actions on the one hand and following stimulation pulses on the other hand.

It is possible, for example, to shorten the time interval for the steps following a stimulus—relative to spontaneous heart actions—by using a predetermined factor (e.g. 2), which is realized in an arrangement according to FIG. 1, for example, by way of an additional signal connection between timing control 12A and the pulse generator of a pacemaker component. Following a stimulus, a detection parameter can furthermore or additionally be adjusted—in particular the amplification of the input stage—to a value that is different from the one following a spontaneous heart action. For this, an additional control connection between pacemaker pulse generator and input stage control unit 23 can be provided for the arrangement according to FIG. 2.

It will be understood that the above description of the present invention is susceptible to various modifications, changes and adaptations, and the same are intended to be comprehended within the meaning and range of equivalents of the appended claims.

What is claimed is:

1. A signal detector for detecting a biosignal with nearly known morphology in a disturbed input signal (ECG) having signal complexes, comprising:

a detector input for detecting the input signal (ECG) with signal complexes and a detector output for emitting a detection signal that indicates the detection of the biosignal in the input signal;

a threshold value discriminator connected with the detector input, said threshold value discriminator comparing the input signal (ECG) with a detection threshold value and outputting to the detector output a high level signal so that the detector output emits the detection signal if the threshold value is exceeded by the input signal;

an amplitude detection device connected to the detector input and to the output of the threshold value discriminator and functions to detect a maximum amplitude of the detected signal complex during a predetermined time window, following the output of the detection signal;

an amplitude memory for storing the maximum amplitude of the detected signal complex, said amplitude memory being connected to the amplitude detection device and having several storage elements for storing a plurality of amplitudes of preceding signal complexes;

an arithmetic unit for calculating a variable lower limit value for the detection threshold value in dependence on the stored amplitudes, said arithmetic unit being connected to said amplitude memory and calculating the variable lower limit by giving a greater weight to the amplitudes of immediately preceding signal complexes than to amplitudes of older signal complexes;

a detector parameter pre-selection circuit that is connected to the arithmetic unit and to the threshold value discriminator, said detector parameter pre-selection circuit determining an initial value for a detector parameter which reflects the sensitivity of the signal detector, the detector parameter determines the detection threshold value by responding to the detection signal and in dependence on the maximum amplitude;

a detector parameter timing circuit connected to the threshold value discriminator for adjusting a predetermined time dependence of the detector parameter and thus also the detection threshold value, said detector parameter timing circuit starts with the initial value of the detector parameter, wherein the predetermined time dependence comprises in a first time domain a step-by-step reduction of the detection threshold value up to at most the lower limit value determined by the arithmetic unit.

2. A signal detector according to claim 1, further comprising a blocking element connected in series before the output, for blocking the emission of another detection signal during a predetermined time interval following a detection signal.

3. A signal detector according to claim 1, further comprising a time step memory assigned to the detection parameter pre-selection circuit, for storing at least one time dependence on the detection threshold value.

4. A signal detector according to claim 1, further comprising a threshold value memory and a second arithmetic unit which is connected to the threshold value memory for changing the detector parameter and thus the detection threshold by a predetermined factor.

5. A signal detector according to claim 1, further comprising an input amplifier having a control input for adjusting an amplification factor, an amplitude classification memory for storing a classification threshold value, designed to differentiate between strong and weak detection events,; and a classification comparator unit connected to the amplitude classification memory and the detector input and indirectly with the input amplifier control input, said classification comparator unit comparing the input signal with the stored classification threshold value and producing a control signal at the input amplifier when the threshold value is exceeded.

6. A signal detector according to claim 1, further comprising a first detection threshold value limiter that is connected to an output of the arithmetic unit.

7. A signal detector according to claim 6, further comprising a second limiter connected in series with the first limiter for limiting the detection threshold value to a fixed predetermined, absolute limit value.

8. A signal detector according to claim 1, wherein the arithmetic unit calculates an upper limit value for the detection threshold value and the predetermined time dependence further comprises in a second time domain a step-by-step increase with predetermined steps of the detection threshold value up to at most the upper limit value determined by the arithmetic unit in dependence on the maximum amplitude of the immediately preceding signal complex.

* * * * *